(12) United States Patent
Terakura (10) Patent No.: US 7,285,115 B2
(45) Date of Patent: Oct. 23, 2007

(54) REMOTE CONTROLLED MEDICAL INSTRUMENT

(75) Inventor: Seiji Terakura, Higashiosaka (JP)

(73) Assignee: Vectronics Corporation, Higa Shiosaka-ski (JP)

( * ) Notice: Subject to any disclaimer, the term of this patent is extended or adjusted under 35 U.S.C. 154(b) by 73 days.

(21) Appl. No.: 10/517,837

(22) PCT Filed: Jul. 2, 2003

(86) PCT No.: PCT/JP03/08441

§ 371 (c)(1),
(2), (4) Date: Dec. 15, 2004

(87) PCT Pub. No.: WO2004/004585

PCT Pub. Date: Jan. 15, 2004

(65) Prior Publication Data

US 2005/0209590 A1    Sep. 22, 2005

(30) Foreign Application Priority Data

Jul. 3, 2002    (JP)    ............................ 2002-195041

(51) Int. Cl.
*A61B 17/00*    (2006.01)
*A61B 18/18*    (2006.01)

(52) U.S. Cl. ............................. 606/1; 606/47; 606/41; 606/113

(58) Field of Classification Search ............... 606/1, 606/41, 47–50, 113, 114; 600/562, 564
See application file for complete search history.

(56) References Cited

U.S. PATENT DOCUMENTS 4,905,691 A    3/1990    Rydell
5,152,779 A    10/1992    Sanagi
5,158,561 A    10/1992    Rydell et al.
5,766,184 A    6/1998    Matsuno et al.
5,779,686 A    7/1998    Sato et al.

FOREIGN PATENT DOCUMENTS

| EP | 0 738 501 A1 | 10/1996 |
|---|---|---|
| JP | 05-337130 A | 12/1993 |
| JP | 06-9622 Y2 | 3/1994 |
| JP | 7-95982 A | 4/1995 |
| JP | 8-126648 A | 5/1996 |
| JP | 10-137261 A | 5/1998 |

*Primary Examiner*—Michael Peffley
(74) *Attorney, Agent, or Firm*—Birch, Stewart, Kolasch & Birch, LLP (57) ABSTRACT

A wire section (1) inserted into a patient includes a wire (4) connected with a snare (3) at the front end thereof, and an outer tube (8) which retractably passes the wire (4) and the snare (3) therein. A remote control section (2) not inserted into the patient's body includes a bar-like main body (9) with a hollow inside; an operating member (11) connected to the main body (9) so as to be slidable in L and R direction and sled to enter or exit the snare (3) into and from the outer tube (8); and a pinching mechanism (15) built in the main body (9) and connected to the operating member (11) for detachably pinching the pipe (6) connected to the rear end of the wire (4). The wire section (1) and the remote control section (2) are connected when the pipe (6) is pinched by the pinching mechanism (15), and the wire section (1) and the remote control section (2) are separated when the pipe (6) is released from the pinching mechanism (15).

14 Claims, 11 Drawing Sheets

REMOTE CONTROLLED MEDICAL INSTRUMENT

TECHNICAL FIELD

The present invention relates to a configuration of a remote controlled medical instrument for performing procedures such as, polyp resection.

BACKGROUND ART

A remote controlled medical instrument for remote controlling an actuator inserted into the body and treating an object in the body includes a polypectomy instrument for resecting the polyp formed in the body, a body tissue collecting instrument for collecting a malignant or benign tissue of the body and an internal foreign object extracting instrument for extracting a foreign object taken inside the body.

Figure 10:
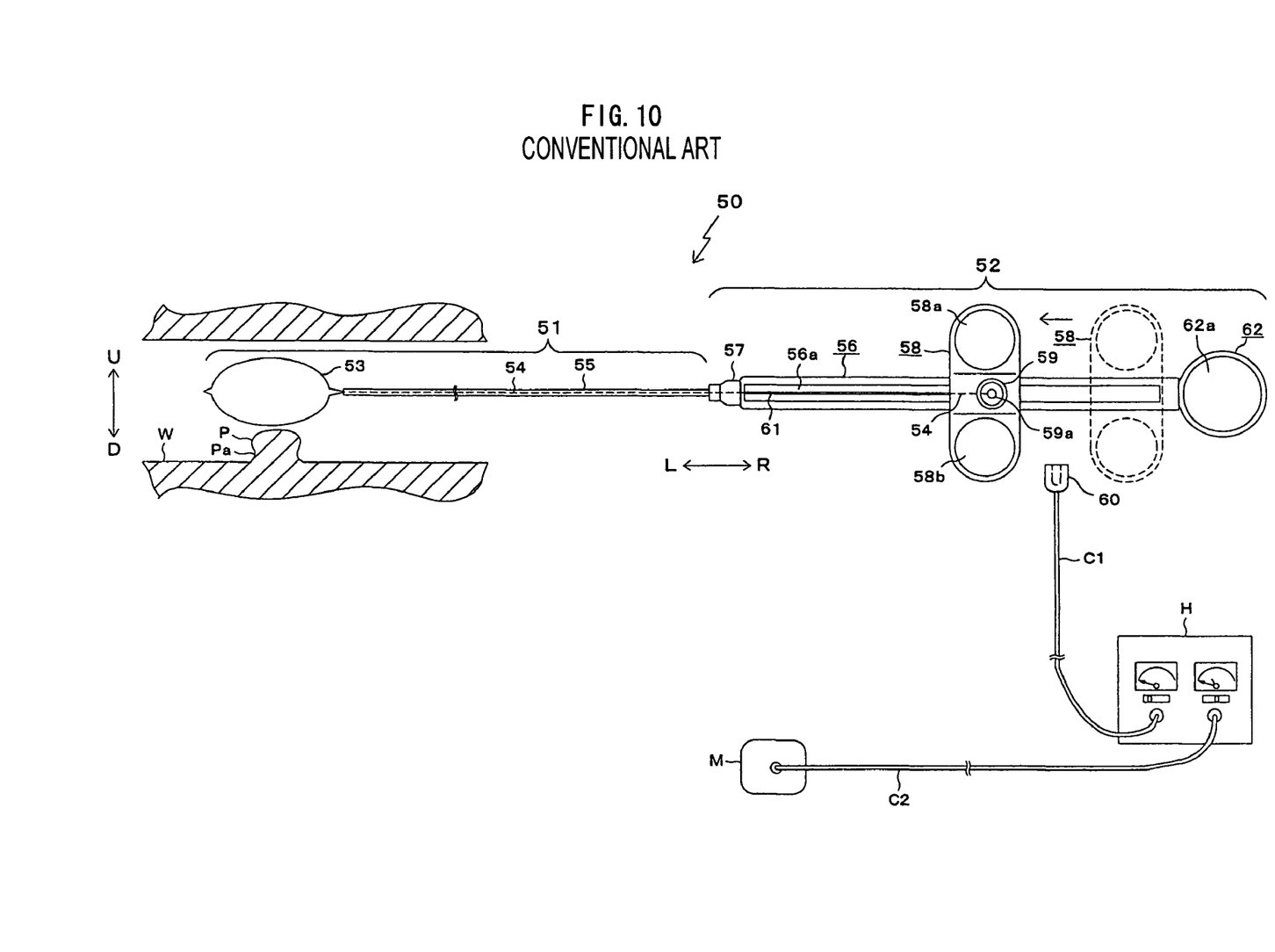
FIG. 10 is a view showing a conventional polypectomy instrument.

The polypectomy instrument, serving by way of example as the above remote controlled medical instrument, conventionally includes a monopolar type and a bipolar type. The monopolar type includes instruments such as that disclosed in Japanese Laid-Open Patent Publication No. 05-337130, and the bipolar type includes instruments such as that disclosed in Japanese Laid-Open Patent Publication No. 10-137261. FIG. 10 is a view showing the above mentioned monopolar polypectomy instrument. In FIG. 10, the polypectomy instrument 50 includes a wire section 51 inserted into the stomach or the intestine through an endoscope, and a remote control section 52 with which the doctors performing the surgery control the wire section 51 outside of the body. H is a high-frequency generator for flowing high-frequency current to the polypectomy instrument 50.

In the wire section 51, 53 refers to a snare serving as an actuator for resecting the polyp P formed at the wall W of the stomach or the intestine (the intestine herein). The snare 53 is an electrode formed by forming a steel stranded wire into a loop shape, and a high-frequency current is flowed out from the high-frequency generator H, as hereinafter described. 54 is a wire made of a steel stranded wire with the snare 53 coupled to the front end, and the rear end of the wire 54 is coupled to the remote control section 52. 55 is a tube through which the wire 54 and the snare 53 pass in a freely entering and exiting manner and is made of a flexible plastic. Here, only the wire 54 is passed through the tube 55, but by pulling the wire 54 in the R direction, the snare 53 is deformed and accommodated inside the tube 55.

In the remote control section 52, 56 is a rod-shaped main body having a hollow inside, and a slit 56a extending in the longitudinal direction L and R of the main body 56 is formed at the side face. A cap 57 for holding the rear end of the tube 55 to the front end of the main body 56 is attached to the front end (L direction side) of the main body 56, and the wire 54 is passed through the cap 57. 58 is an operating member slidably coupled to the main body 56 in the L and R direction, and is formed with finger inserting holes 58a, 58b through which the forefinger and the middle finger are inserted. 59 is a male jack coupled to the operating member 58, and the rear end of the wire 54 is coupled to the root of a terminal 59a at the center. Thus, when the operating member 58 is slide operated in the L and R direction, the wire 54 coupled to the jack 59 is moved in the L and R direction, causing the snare 53 to project out from the inside of the tube 55 or retract inside the tube 55. Further, the jack 59 is fitted with a female jack 60, and is thereby connected to the high-frequency generator H by way of a cable C1. The high-frequency current generated at the high-frequency generator H thereby flows out through the cable C1 and the jacks 60, 59 to the wire 54, and from the wire 54 to the snare 53. M is an external electrode attached to the abdomen or the buttocks of the patient, and is connected to the high-frequency generator H by way of a cable C2. 61 is a pipe coupled to the operating member 58, and is arranged inside the main body 56. The pipe 61 passes the wire 54 therein and leads it to the operating member 58. 62 is a finger holder coupled to the rear end (R direction side) of the main body 56, and is formed with a finger inserting hole 62a through which the thumb is inserted. When the thumb is inserted into the finger inserting hole 62a, and the forefinger and the middle finger are inserted into the finger inserting holes 58a, 58b of the above mentioned operating member 58, the operating member 58 is slide operated in the L and R direction by the forefinger and the middle finger while holding the main body 56.

The steps of resecting the polyp P formed at the wall W of the intestine and the operations of each part in the above polypectomy instrument 50 will now be explained. First, two jacks 59, 60 are fitted together, and the external electrode M is attached to the abdomen or the buttocks of the patient. Next, the wire section 51 is inserted into the intestine of the patient with the endoscope (not shown). Here, the operating member 58 is sled to a position shown with a dotted line, the pipe 61 and the wire 54 are pulled in the R direction, and the snare 53 is retracted inside the tube 55. When the front end of the wire section 51 is inserted to a location where the polyp P is located, the operating member 58 is sled to a position shown with a solid line. The pipe 61 and the wire 54 are thereby pushed in the L direction, causing the snare 53 to project out from the inside of the tube 55, and the projected snare 53 then encircles the base Pa of the polyp P. Here, in FIG. 10, since the projecting direction (U direction herein) of the polyp P and the loop surface of the snare 53 are parallel, even if the snare 53 is moved in the D direction, the snare 53 does not encircle the polyp P, and thus the polyp P is rotated with the entire intestine with respect to the snare 53 by having the patient change the body position to have the projecting direction of the polyp P perpendicular to the loop surface of the snare 53, and the snare 53 then encircles the polyp P.

Figure 11:
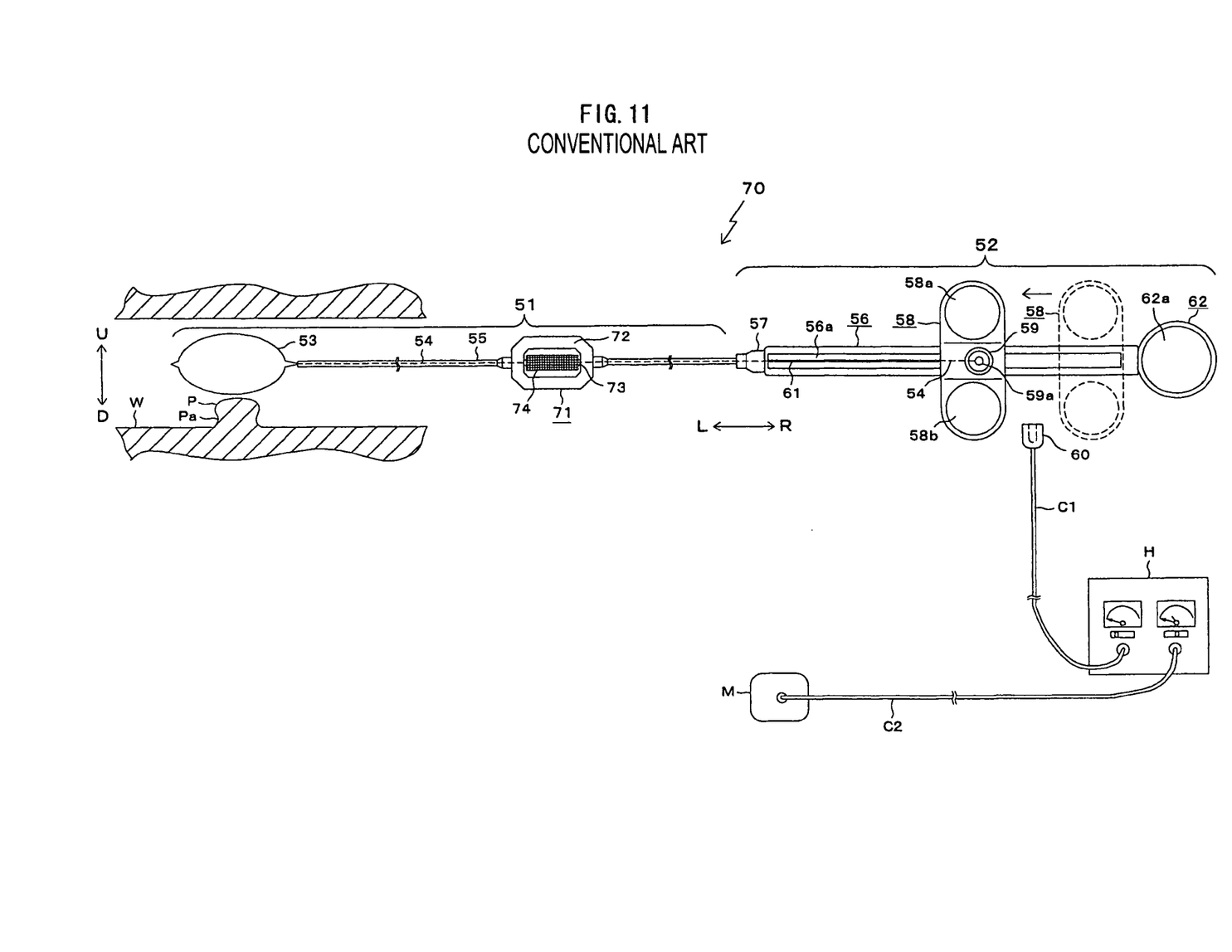
FIG. 11 is a view showing another conventional polypectomy instrument.

Further, when a polypectomy instrument 70 equipped with a rotating mechanism part 71 is used as shown in FIG. 11, the snare 53 easily encircles the polyp P without having the patient change the body position. The reference characters of each part shown in FIG. 11 are the same for parts similar to those in FIG. 10. In FIG. 11, the rotating mechanism part 71 is arranged on the middle of the wire section 51, and is configured from a grip 72 gripped by the hand, a supporting pipe 73 rotatably supported at the middle of the grip 72, and a roller 74 fixed to the peripheral surface of the supporting pipe 73. The supporting pipe 73 passes the wire 54 therein and holds the wire 54. Due to such rotating mechanism part 71, by rotating the roller 74 with the axis of the supporting pipe 73 as the rotating center, the supporting pipe 73 and the wire 54 are rotated in the same direction as the roller 74, and the rotational torque of the wire 54 is transmitted to the snare 53, thus rotating the snare 53 in the same direction as the roller 74. Therefore, the snare 53 is rotated with respect to the polyp P without having the patient change the body position to have the projecting direction of the polyp P perpendicular to the loop surface of the snare 53, and the snare 53 then encircles the polyp P. Further, the surgery can be performed without having the patient change the body position, and thus the load on the patient can be removed.

When the snare 53 encircles the polyp P as above, the high-frequency current is flowed out from the high-frequency generator H to the snare 53 through the wire 54. Thus, the high-frequency current is conducted from the base Pa of the polyp P encircled by the snare 53 through the body of the patient and to the external electrode M, and heat generation as well as burning occurs at a portion of the polyp P having the smallest cross sectional area. Subsequently, when the operating member 58 is gradually sled to the R direction, the pipe 61 and the wire 54 are pulled in the R direction, causing the snare 53 to gradually retract inside the tube 55, and thus the base Pa of the polyp P is tightened by the snare 53. Finally, the base Pa of the polyp is burnt off by the burning by the high-frequency current and the tightening force of the snare 53, and the polyp P is resected from the wall W of the intestine.

In the conventional polypectomy instrument 50, 70, the wire section 51 inserted into the body of the patient is discarded after the surgery in view of infection of disease and hygienic problems. However, since the remote control section 52 and the rotating mechanism part 71 are integrally coupled to the wire section 51, the remote control section 52 and the rotating mechanism part 71 not inserted into the body of the patient are also discarded with the wire section 51, and thus the entire instrument 50, 70 is disposable. This is a great waste when using the instrument, and is a factor in the increase of facility cost of hospitals and the like.

DISCLOSURE OF THE INVENTION

The present invention aims to overcome the above problems, and aims to provide a remote controlled medical instrument in which the part not inserted into the body of the patient can be reused.

In the remote controlled medical instrument according to the present invention, the wire section includes a wire coupled with an actuator at the front end thereof, and a tube for passing the wire and the actuator therein in a freely entering and exiting manner; and the remote control section includes a rod-shaped main body having a hollow inside, an operating member, coupled to the main body so as to be slidable in a longitudinal direction of the main body, for entering and exiting the actuator into and from the tube by sliding, and a pinching mechanism, built in the main body and coupled to the operating member, for detachably pinching a rear end of the wire.

The coupling and separation of the wire section inserted into the body of the patient and the remote control section not inserted into the body of the patient are thereby freely carried out, and thus only the wire section is discarded and replaced with a new one each time the surgery is performed and thus the remote control section can be reused. As a result, the wasteful use of the entire instrument can be eliminated, and the facility cost necessary for surgery can be kept low.

Further, in the remote controlled medical instrument according to the present invention, the pinching mechanism is configured by a coupling member for coupling the operating member and the wire, a clip member, arranged in the coupling member, for pinching the wire, and a sliding member sliding independently from the coupling member in the longitudinal direction of the main body, where the clip member is preferably configured so as to pinch the wire in conjunction with the sliding of the sliding member in one direction and to release the wire in conjunction with the sliding of the sliding member in the other direction.

With the sliding operation of the sliding member, the clip member detachably pinches the wire, the operating member and the wire are coupled or separated by way of the coupling member, and thus the detachment operation of the wire to the operating member can be easily carried out.

In addition, in the remote controlled medical instrument according to the present invention, the above mentioned pinching mechanism is rotatably built in the main body with an axis of the longitudinal direction of the main body as a rotating center, and can be configured so as to rotate the pinched wire and the actuator in conjunction with each other.

Thus, the pinching mechanism built in the remote control section also functions as a rotating mechanism for rotating the actuator coupled to the front end of the wire, and thus by reusing the remote control section each time the surgery is performed, the rotating mechanism is also reused.

BEST MODE FOR CARRYING OUT THE INVENTION

Figure 1:
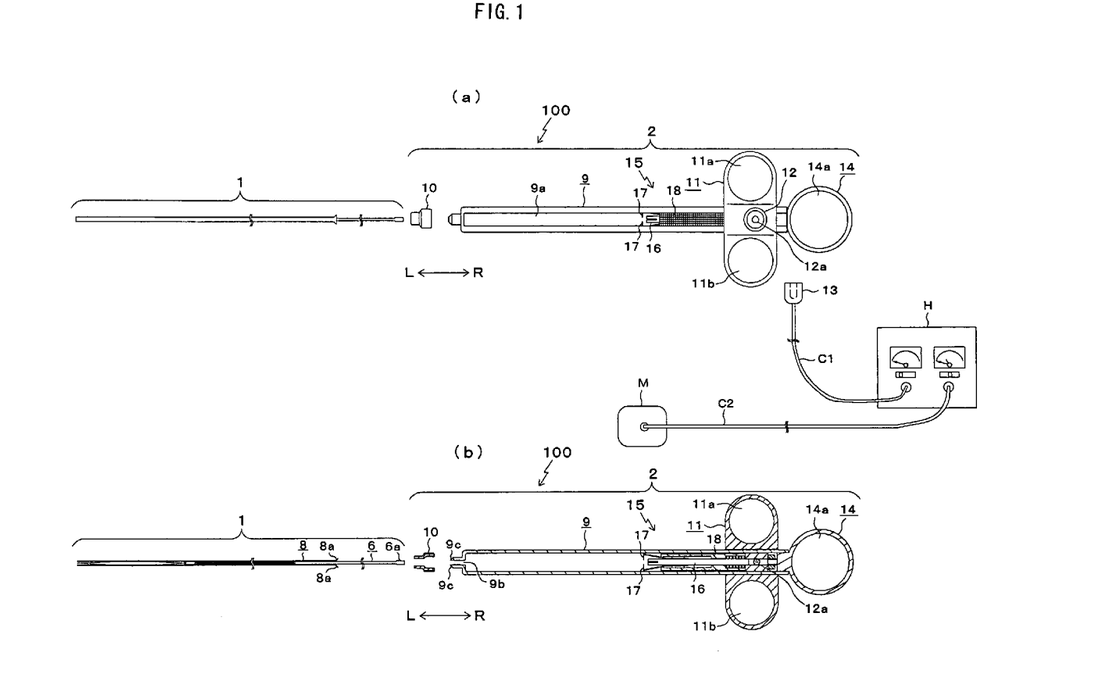
FIG. 1 is a view showing an entire polypectomy instrument, by way of example, of a remote controlled medical instrument according to the present invention.
Figure 2:
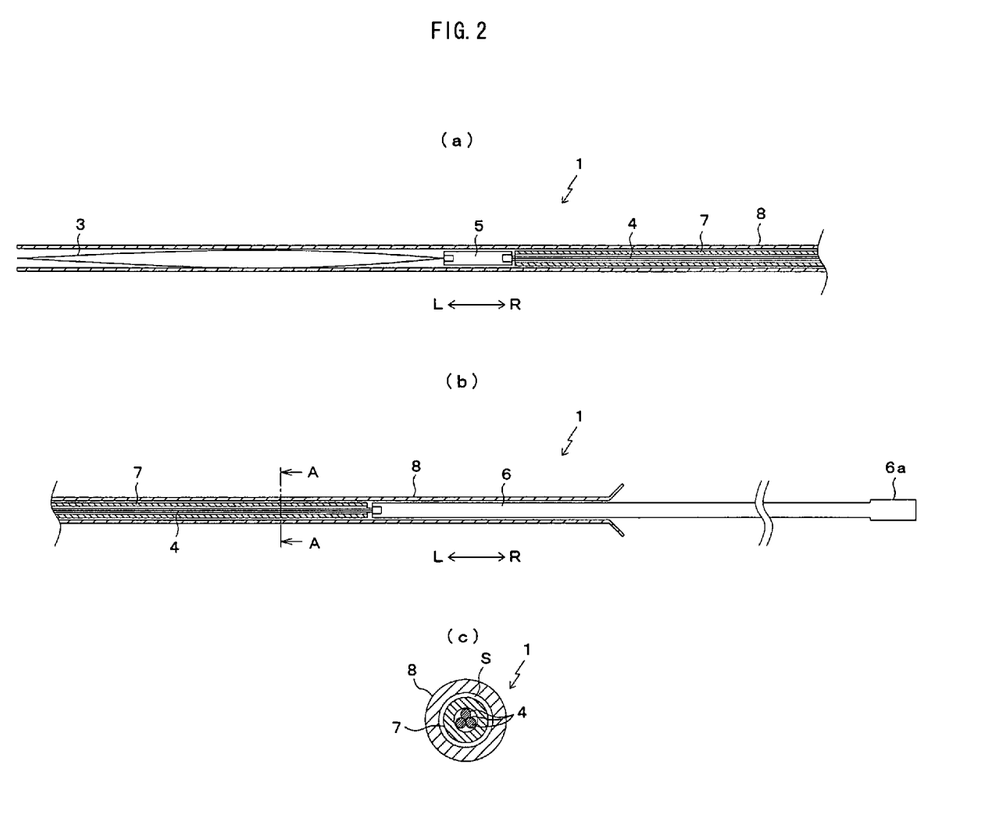
FIG. 2 is an enlarged view of a wire section of the instrument.
Figure 3:
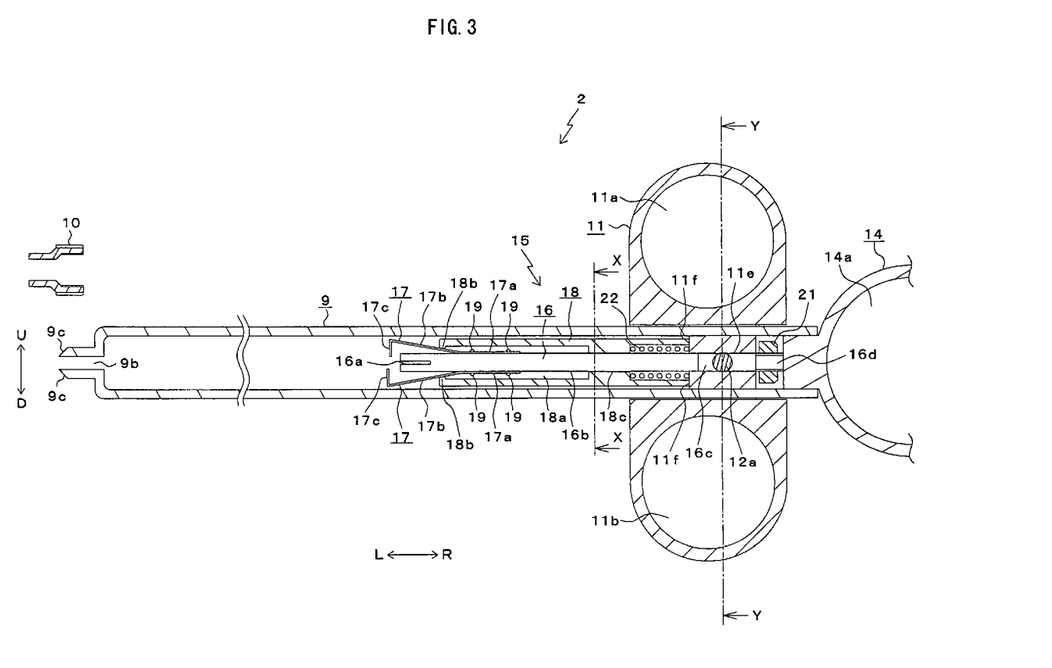
FIG. 3 is an enlarged view of a remote control section of the instrument.
Figure 4:
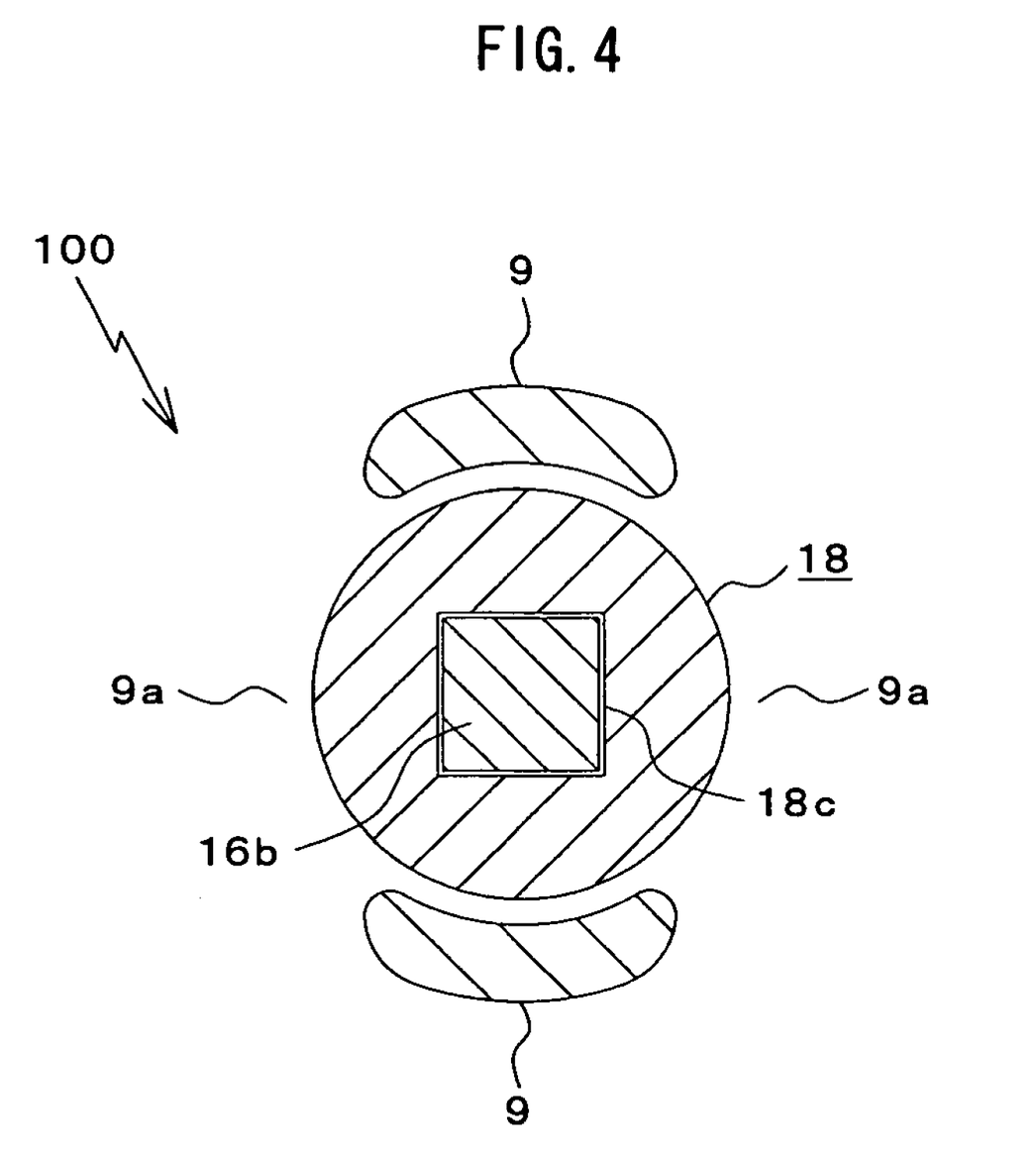
FIG. 4 is a cross sectional view taken along line X-X in FIG. 3.
Figure 5:
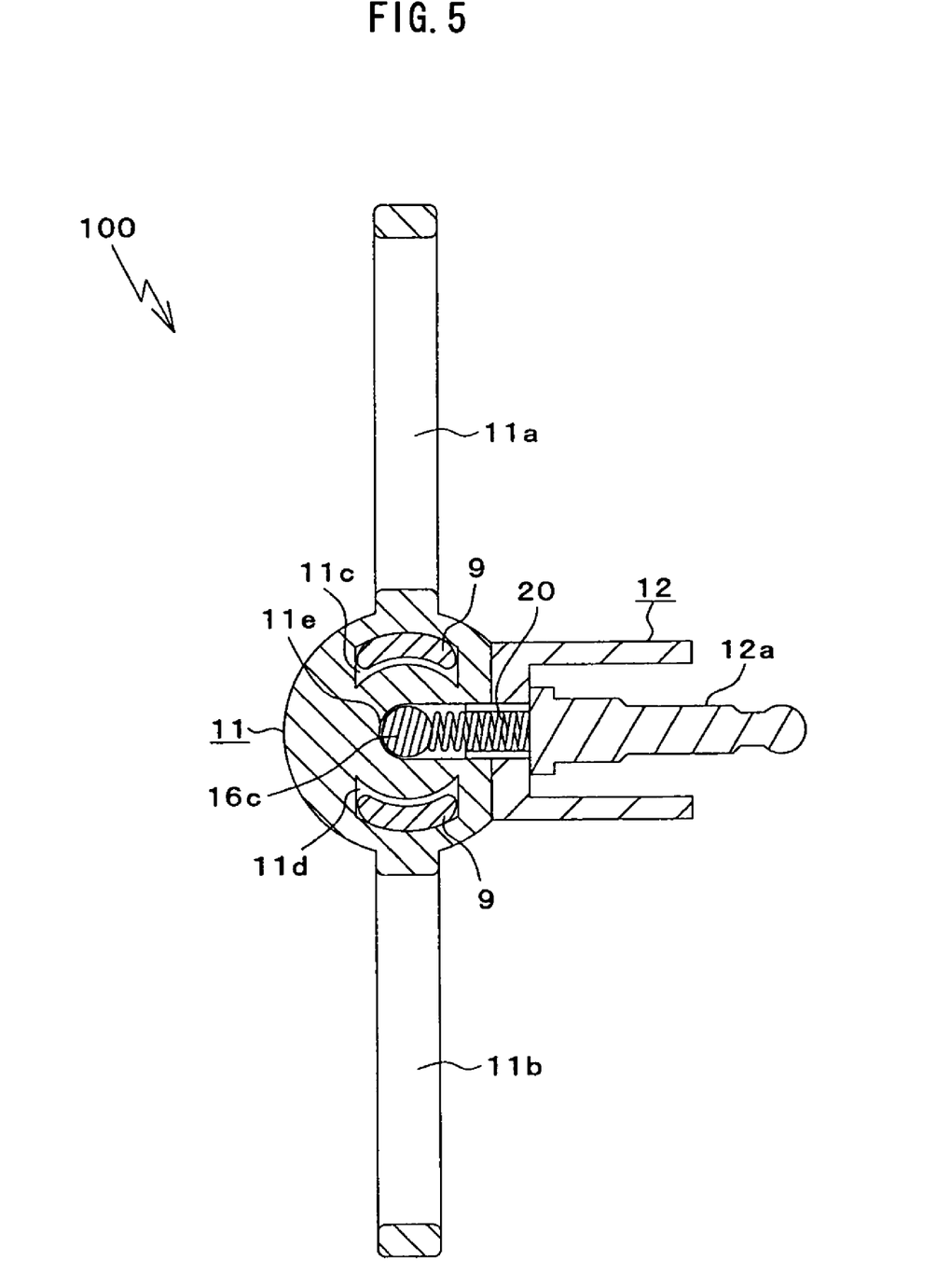
FIG. 5 is a cross sectional view taken along line Y-Y in FIG. 3.
Figure 6:
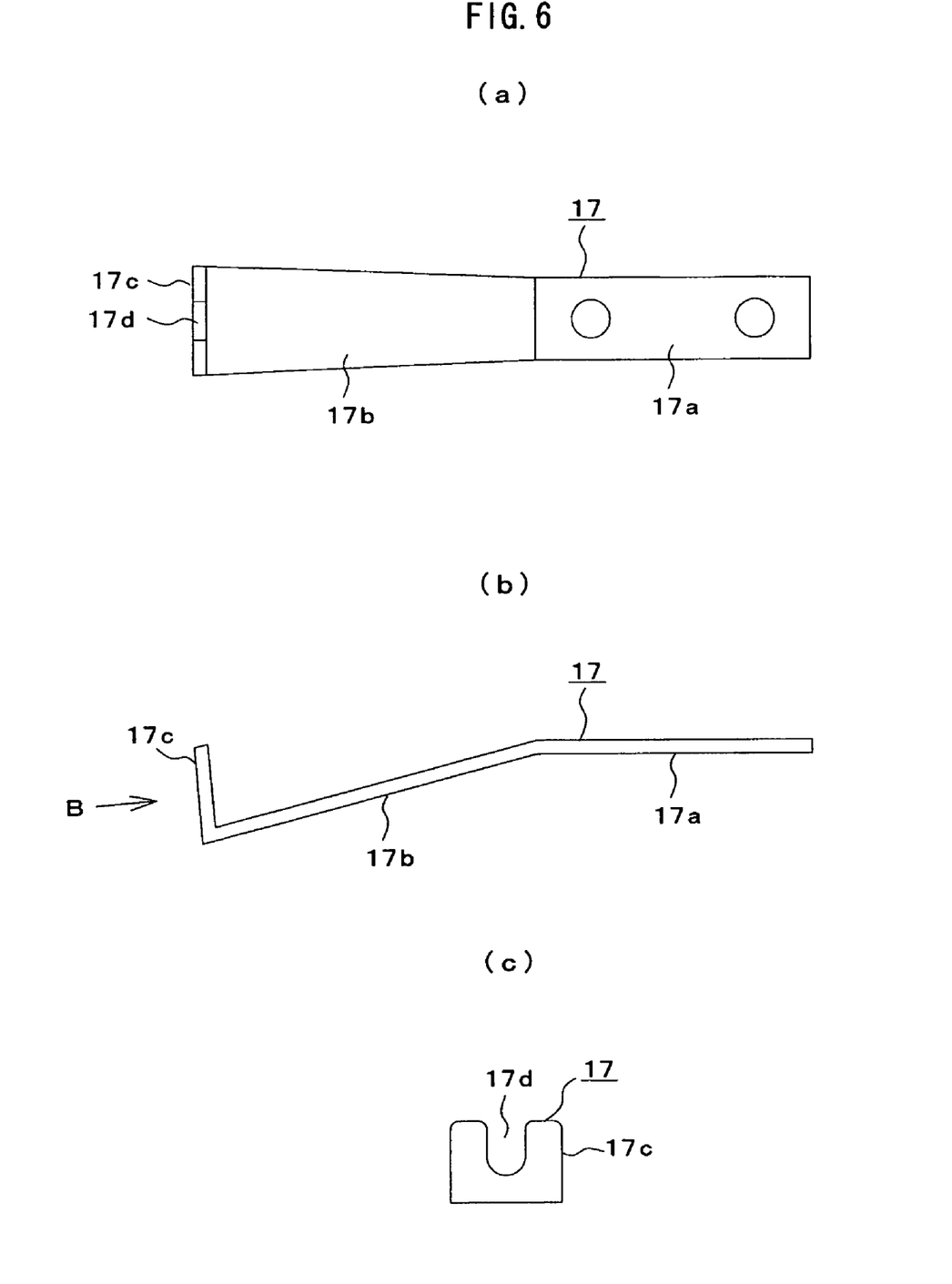
FIG. 6 is a view showing a clip member of the polypectomy instrument.

The embodiment of the present invention will now be described with reference to the drawings. FIG. 1 through FIG. 6 are views explaining a configuration of a remote controlled medical instrument according to the present invention. FIG. 1 is a view showing the entire polypectomy instrument as one example of a remote controlled medical instrument, where (a) is an outline view, and (b) is a cross sectional view. FIG. 2 is an enlarged cross sectional view of a wire section in the instrument, where (a) is a cross sectional view of a front end, (b) is a cross sectional view of a rear end, and (c) is a cross sectional view taken along line A-A in (b). FIG. 3 is an enlarged cross sectional view of a remote control section in the instrument. FIG. 4 is a cross sectional view taken along line X-X in FIG. 3, and FIG. 5 is a cross sectional view taken along line Y-Y in FIG. 3. FIG. 6 is a view showing a clip member in the polypectomy instrument, where (a) is a plan view, (b) is a side view, and (c) is a perspective view seen from the B direction. Here, the reference character of each part in each view is denoted with the same reference character for components similar to those in FIG. 10.

In FIG. 1(a), 100 is the polypectomy instrument, and in the present embodiment, is a monopolar polypectomy instrument. The polypectomy instrument 100 is configured from a wire section 1 inserted into the stomach or the intestine through the endoscope, and a remote control section 2 with which the doctors performing the surgery control the wire section 1 outside of the body. H is a high-frequency generator for flowing high-frequency current to the polypectomy instrument 100.

In the wire section 1, 3 shown in FIG. 2(a) is a snare serving as an actuator for resecting the polyp formed at the wall of the stomach or the intestine. The snare 3 is an electrode formed by forming the steel stranded wire into a loop shape, and the high-frequency current is flowed out from the high-frequency generator H, as hereinafter described. 4 is a wire formed without twisting the three single wires, and the snare 3 is coupled to a front end (L direction side) of the wire 4. A stainless pipe 5 is used for coupling the front end of the wire 4 and the snare 3, and the pipe 5 passes and caulks each the wire 4 and the snare 3 therein. Further, as shown in FIG. 2(b), the rear end (R direction side) of the wire 4 is caulked to a long stainless pipe 6, and a rear end 6a of the pipe 6 is subjected to crush machining and is made flat.

7 is an inner tube for passing the wire 4 therein and is made of a flexible plastic. As shown in FIG. 2(c), the inner tube 7 has an inner diameter to an extent of passing three single wires configuring the wire 4 to regulate the wire 4 from being twisted or bent in the L and R direction in the inside. 8 is an outer tube for passing the snare 3, the inner tube 7, and the pipes 5, 6 therein in a freely entering and exiting manner, and is made of a flexible plastic. The outer tube 8 has an inner diameter greater than the outer diameter of the inner tube 7 and the pipes 5, 6, includes a clearance S between the inner tube 7 and the pipes 5, 6 to allow the inner tube 7 to freely move inside in the L and R direction and in the circumferential direction of the outer tube 8 without bending. Due to such two tubes 7 and 8, the wire 4 is able to freely move inside the outer tube 8 in the L and R direction and in the circumferential direction without bending, and as hereinafter described, the force in the L and R direction and the rotational torque in the circumferential direction transmitted from the remote control section 2 to the wire 4 are transmitted from the wire 4 to the snare 3 without substantially no loss, thus allowing the snare 3 to smoothly move in the L and R direction and in the circumferential direction.

Next, in the remote control section 2, 9 shown in FIG. 1(a) is a rod-shaped main body having a hollow inside, and a slit 9a extending in the longitudinal direction L and R of the main body 9 is formed on the side surface. Here, the rear end (R direction side) of the slit 9a is opened, and thus the main body 9 is formed into a horseshoe shape. As shown in FIG. 1(b), an inserting port 9b for passing the pipe 6 inside the main body 9 is formed at the front end (L direction side) of the main body 9. 10 is a cap attached to the front end of the main body 9, and the cap 10 passes the wire section 1 therein and holds the rear end 8a of the outer tube 8 at a tapered part 9c of the front end of the main body 9. The rear end 8a of the outer tube 8 is opened in a horn shape so as to be easily held at the tapered part 9c of the main body 9.

11 is an operating member, and as shown in FIG. 5, hyperbolic pass-through holes 11c, 11d are formed therein. The main body 9 is passed through the pass-through holes 11c, 11d, thereby slidably coupling the operating member 11 to the main body 9 in the L and R direction. In FIG. 1(a), 11a, 11b are finger inserting holes to which the forefinger and the middle finger are inserted. 12 is a male jack coupled to the operating member 11, and 12a is a terminal of the jack 12. The jack 12 is fitted to a female jack 13, and is thereby connected to the high-frequency generator H by way of the cable C1. M is an external electrode attached to the abdomen or the buttocks of the patient, and is connected to the high-frequency generator H by way of the cable C2. 14 is a finger holder coupled to the rear end of the main body 9, and a finger inserting hole 14a to which the thumb is inserted is formed in the finger holder 14. When the thumb is inserted into the finger inserting hole 14a, and the forefinger and the middle finger are inserted into the finger inserting holes 11a, 11b of the above mentioned operating member 11, the operating member 11 is slide operated in the L and R direction with the forefinger and the middle finger while holding the main body 9.

In FIG. 3, 15 is a pinching mechanism built in the main body 9, and the pinching mechanism 15 is configured by a coupling member 16 for coupling the rear end 6a of the pipe 6 (FIG. 2) and the operating member 11, a pair of clip members 17 coupled to the coupling member 16, and a sliding member 18 sliding independently from the operating member 11 in the L and R direction. The coupling member 16 and the clip member 17 are made of stainless steel and the slide member 18 is made of synthetic resin. The pinching mechanism 15 also functions as a rotating mechanism for rotating the wire 4 (FIG. 2) and the snare 3 (FIG. 2) coupled to the front end of the wire 4.

A groove 16a to which the rear end 6a of the pipe 6 is inserted is formed at the front end of the coupling member 16, and the pair of clip members 17 is arranged in the vertical direction U, D of the groove 16a. The clip member 17 is configured from a plate spring of a shape shown in FIG. 6, and a flat part 17a is coupled to a base part 16b of the coupling member 16 by a rivet 19. Further, a notch 17d as shown in FIG. 6(c) is formed at a pinching part 17c at the front end of the clip member 17. The clip member 17 pinches the pipe 6 with the notch 17d, as hereinafter described, and couples the pipe 6 to the coupling member 16.

In FIG. 3, a contacting part 16c passing through a communicating hole 11e of the operating member 11 is formed on the R direction side of the base part 16b of the coupling member 16. As shown in FIG. 5, the contacting part 16c has a circular cross section, and contacts the terminal 12a of the jack 12 by way of a spring 20. Thus, the high-frequency current flowing into the jack 12 from the high-frequency generator H is flowed through the terminal 12a and the spring 20 into the coupling member 16 from the contacting part 16c. Further, as shown in FIG. 3, a threaded part 16d is formed on the R direction side of the contacting part 16c. The threaded part 16d is projected out from the communicating hole 11e of the operating member 11 and is fastened by a nut 21. The movement of the coupling member 16 to the L direction is regulated by the nut 21, but since the nut 21 is not fixed to the operating member 11, the rotation of the coupling member 16 in the circumferential direction is not regulated.

The sliding member 18 is, as shown in FIG. 3, arranged between an inner wall 11f of the operating member 11 and a slanted part 17b of the clip member 17, and is biased in the L direction by a spring 22. The sliding member 18 is exposed from the slit 9a of the main body 9, as shown in FIG. 1(a) and FIG. 4, and thus can be sled to the L and R direction by operating with the finger. Further, an accommodating space 18a for accommodating the clip member 17 is formed inside the sliding member 18. 18b is a projection provided at the front end of the accommodating space 18a. When the sliding member 18 is sled in the L direction, the sliding member 18 is separated away from the inner wall 11f of the operating member 11, and the clip member 17 and the groove 16a of the coupling member 16 are interiorly accommodated in the accommodating space 18a. Here, the slanted parts 17b of the pair of clip members 17 are pushed towards the coupling member 16 side by the projection 18b, and each pinching part 17c closes and overlaps. Further, a square hole 18c for passing the base part 16b of the coupling member 16 having a square cross section is formed inside the sliding member 18, as shown in FIG. 4. Thus, when the sliding member 18 exposed from the slit 9a of the main body 9 is rotated with the finger with the axis of the longitudinal direction L and R of the main body 9 as the rotation center, the coupling member 16 and the clip member 17 are integrally rotated in conjunction therewith. A vertical and horizontal knurl machining is performed on the surface of the sliding member 18, as shown in FIG. 1. The sliding member 18 is thereby easily rotated and sled.

Figure 7:
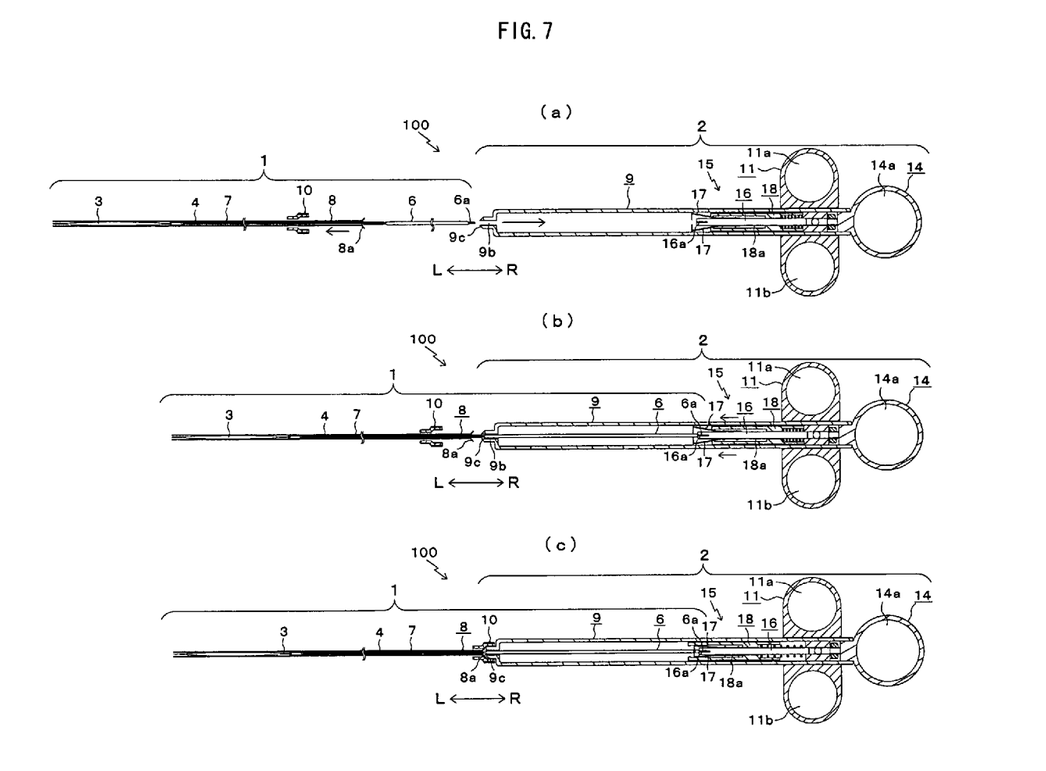
FIG. 7 is a view explaining steps for coupling the wire section and the remote control section of the instrument.
Figure 8:
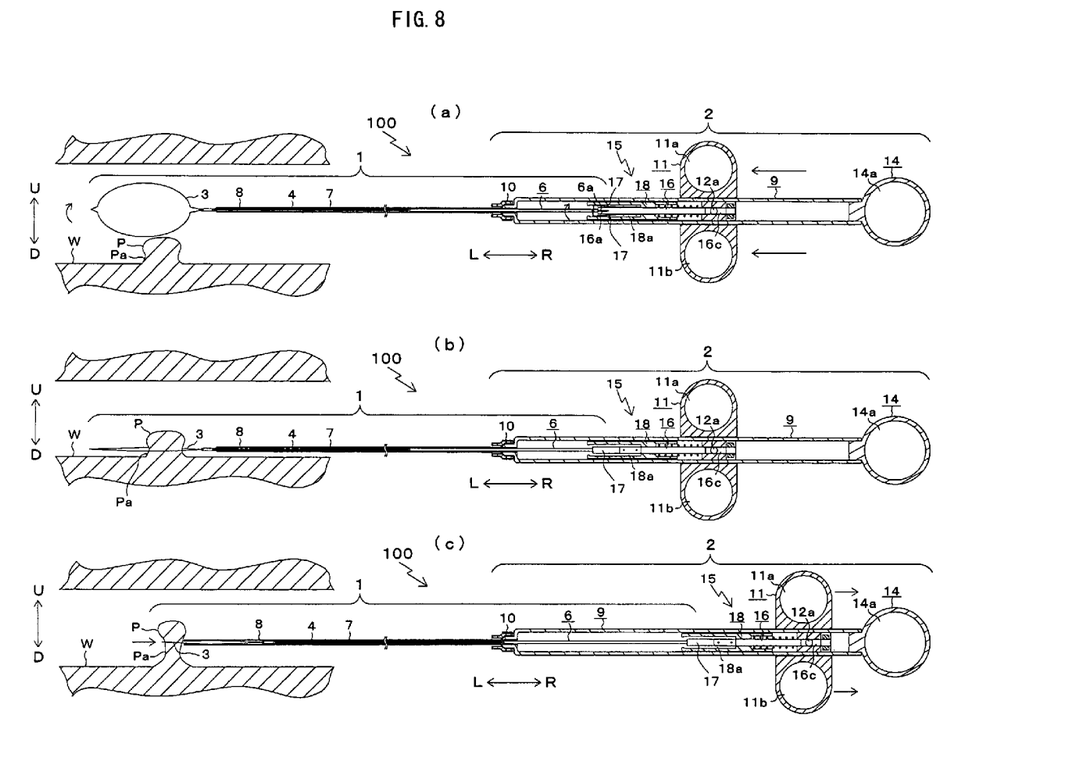
FIG. 8 is a view explaining steps for resecting the polyp of the instrument.
Figure 9:
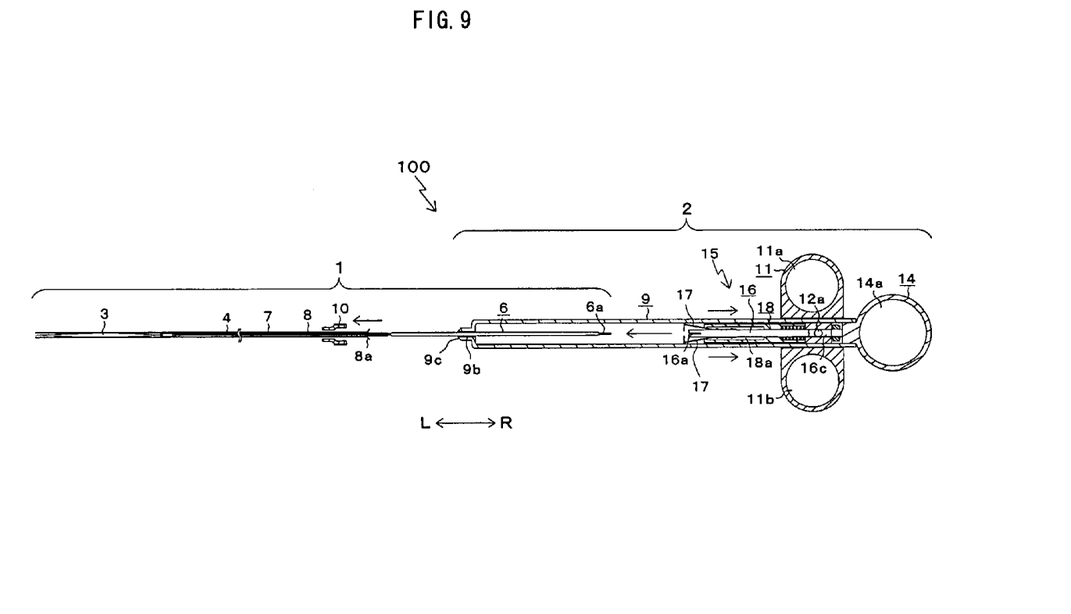
FIG. 9 is a view explaining steps for separating the wire section and the remote control section of the instrument.

The steps for resecting the polyp P formed at the wall W of the intestine and the operations of each part in the above mentioned polypectomy instrument 100 will now be described with reference to FIG. 7 through FIG. 9. FIG. 7 is a view explaining a coupling step of the wire section 1 and the remote control section 2, FIG. 8 is a view explaining a resecting step of the polyp P, and FIG. 9 is a view explaining a separating step of the wire section 1 and the remote control section 2.

First, the wire section 1 and the remote control section 2 are coupled and the polypectomy instrument 100 is assembled. In FIG. 7(a), the wire section 1 is first passed through the cap 10. Here, since the rear end 8a of the outer tube 8 is opened, the front end of the wire section 1 is inserted from the rear end (R direction side) of the cap 10. Next, the pipe 6 is inserted inside the main body 9 from the inserting port 9b, and as shown in FIG. 7(b), the rear end 6a of the pipe 6 is inserted into the groove 16a of the coupling member 16. Further, when the sliding member 18 is sled to the L direction, as shown in FIG. 7(c), the clip member 17 and the groove 16a of the coupling member 16 are inserted in the accommodating space 18a of the sliding member 18. Here, the slanted parts 17b (FIG. 3) of the pair of clip members 17 are pushed towards the coupling member 16 side by the projection 18b of the sliding member 18 and is displaced, and the pinching part 17c (FIG. 3) is closed and overlapped thus pinching the pipe 6 between the pair of notches 17d, and the pipe 6 is coupled to the coupling member 16. The operating member 11 and the wire 4 are thereby coupled by way of the coupling member 16. Subsequently, when the cap 10 is attached to the front end of the main body 9, and the rear end 8a of the outer tube 8 is held between the tapered part 9c of the main body 9 and the cap 10, the wire section 1 and the remote control section 2 are completely coupled, and the assembling of the polypectomy instrument 100 is completed.

Next, the polyp P formed at the wall W of the intestine is resected using the above polypectomy instrument 100. First, the jack 12 (shown in FIG. 1) of the operating member 11 and the jack 13 (shown in FIG. 1) of the high-frequency generator H are fitted together, and the external electrode M (shown in FIG. 1) is attached to the abdomen or the buttocks of the patient. The wire section 1 is then inserted into the intestine of the patient with the endoscope (not shown).

Here, the operating member 11 is at a position of FIG. 7(c), and the snare 3 is retracted inside the outer tube 8. When the front end of the wire section 1 is inserted to a location where the polyp P is located, the operating member 11 is sled in the L direction, as shown in FIG. 8(a). The coupling member 16 and the pipe 6 are thereby pushed in the L direction, and thus the inner tube 7 and the wire 4 are also pushed in the L direction by such pushing force, and the snare 3 is projected out from the inside of the outer tube 8.

After the snare 3 is completely projected out from the inside of the outer tube 8, the snare 3 encircls the base Pa of the polyp P. Here, in FIG. 8(a), since the projecting direction (here, U direction) of the polyp P and the loop surface of the snare 3 are parallel, even if the snare 3 is moved in the D direction, the snare 3 does not encircle the polyp P, and thus the sliding member 18 is operated with the fingers to be rotated with the axis of the longitudinal direction L and R of the main body 9 as the rotating center. When the sliding member 18 is rotated, the coupling member 16 and the clip member 17 are integrally rotated in conjunction therewith, and the rotational torque thereof is transmitted to the wire 4 through the pipe 6, and is transmitted from the wire 4 to the snare 3. Due to the rotational torque transmitted from the wire 4, the snare 3 is rotated in the same direction as the sliding member 18. When the snare 3 is rotated in this way, the loop surface of the snare 3 becomes perpendicular to the projecting direction of the polyp P and thus allows the snare 3 to encircle the polyp P, as shown in FIG. 8(b). Even if the coupling member 16 is rotated with the sliding member 18, since the cross section of the contacting part 16c of the coupling member 16 is circular (FIG. 5), the contact of the coupling member 16 and the terminal 12a is maintained.

When the snare 3 encircles the polyp P, the high-frequency current is flowed from the high-frequency generator H through the wire 4 to the snare 3. Here, as shown in FIG. 7(c), the pipe 6 is pinched by the clip members 17 and attached to the coupling member 16, and thus when the high-frequency current is flowed from the high-frequency generator H to the cable C1, the high-frequency current is flowed through the jacks 12, 13 and the spring 20 to the coupling member 17, and is flowed from the coupling member 16 through the pipe 6 and the wire 4 to the snare 3. The high-frequency current is thereby flowed from the base Pa of the polyp P encircled by the snare 3 through the body of the patient to the external electrode M, and heat generation as well as burning occurs at the part of the polyp P with the smallest cross sectional area. Subsequently, when the operating member 11 is gradually sled in the R direction, the coupling member 16 and the pipe 6 are pulled in the R direction, and thus the inner tube 7 and the wire 4 are also pulled in the R direction by the pulling force, and the snare 3 is gradually retracted to the inside of the outer tube 8. When the snare 3 is gradually retracted to the inside of the outer tube 8, the base Pa of the polyp P is tightened by the snare 3, as shown in FIG. 8(c). Finally, the base Pa of the polyp P is burnt off by the burning by the high-frequency current and the tightening force of the snare 3, and the polyp P is resected from the wall W of the intestine. Subsequently, the cut off polyp P is naturally discharged outside the body, or extracted outside the body by a separate remote controlled medical instrument in which a basket shaped grasping forceps serving as an actuator is coupled to the tip.

When the polyp P is cut off from the wall W of the intestine, the operating member 11 is sled maximally in the R direction. The coupling member 16 and the pipe 6 are thereby pulled in the R direction, and the inner tube 7 and the wire 4 are pulled in the R direction, and the snare 3 is retracted to the inside of the outer tube 8.

Subsequently, the wire section 1 is pulled out from the intestine of the patient. Further, the fitting of the jack 13 of the high-frequency generator H and the jack 12 of the operating member 11 is released, and the external electrode M is also removed from the abdomen or the buttocks of the patient. When the wire section 1 is pulled out of the body, the sliding member 18 is sled in the R direction, and the clip member 17 and the groove 16a of the coupling member 16 are projected out from the accommodating space 18a of the sliding member 18, as shown in FIG. 9. Here, the slanted parts 17b (FIG. 3) of the pair of clip members 17 are displaced to the main body 9 side by an elastic force of the clip member 17, thus causing the pinching part 17c (FIG. 3) to open, and the pipe 6 pinched between the pair of notches 17d (FIG. 6) is released, and the pipe 6 becomes separable from the coupling member 16. The cap 10 is removed from the front end of the main body 9, and as the wire section 1 is pulled in the L direction, the rear end 6a of the pipe 6 is broken away from the groove 16a of the coupling member 16, and the operating member 11 and the wire 4 are separated. Further, when the pipe 6 is pulled out from the inside of the main body 9, the wire section 1 and the remote control section 2 are completely separated. Subsequently, only the separated wire section 1 is discarded, and by coupling a new wire section 1 again to the remote control section 2, the remote control section 2 can be reused.

When configured as above, the coupling and separation of the wire section 1 inserted into the body of the patient and the remote control section 2 not inserted into the body of the patient can be freely carried out, and thus only the wire section 1 is discarded and replaced with a new one each time the surgery is performed and the remote control section 2 can be reused. As a result, a wasteful use of the entire polypectomy instrument 100 can be eliminated, and the facility cost necessary for the surgery can be kept low. Further, with the sliding operation of the sliding member 18, the clip member 17 detachably pinches the pipe 6 coupled with the wire 4, and the operating member 11 and the wire 4 are coupled or separated by way of the coupling member 16, and thus the attachment or detachment of the wire 4 to the operating member 11 can be easily carried out. Further, since the pinching mechanism 15 configured from the coupling member 16, the clip member 17 and the sliding member 18 also functions as a rotating mechanism for rotating the snare 3 coupled to the front end of the wire 4, the rotating mechanism can be also reused by reusing the remote control section 2 each time the surgery is performed.

In the above mentioned embodiment, a case in which the wire 4 and the operating member 11 are coupled or separated by way of the pipe 6 and the coupling member 16 by detachably pinching the pipe 6 coupled to the rear end of the wire 4 with the clip member 17 is given as an example, but the present invention is not limited thereto, and the wire 4 and the operating member 11 may be coupled or separated by way of the coupling member 16 by detachably pinching the rear end of the wire 4 directly with the clip member 17. In this case, to easily pinch the rear end of the wire 4 with the clip member 17, the rear ends of the three single wires configuring the wire 4 are preferably caulked with a short pipe or is subjected to machining such as connection by soldering.

In the above mentioned embodiment, a case in which the pinching mechanism 15 configured from the coupling member 16, the clip member 17, and the sliding member 18 is adopted as a pinching mechanism for detachably pinching the rear end of the wire 4 is given as an example, but the present invention is not limited thereto. The pinching mechanism may also include, in addition, a mechanism in which a contacting terminal having an elastic force is embedded in the groove 16a of the front end of the coupling member 16 to detachably pinch the front end 6a of the pipe 6 to such contacting terminal, or a mechanism in which a clip terminal connected to the terminal 12a of the jack 12 with a lead wire is coupled to the front end of the operating member 11 to detachably pinch the wire 4 directly with such clip terminal. That is, the mechanism may be of any kind as long as the rear end of the wire 4 is detachably pinched, and the wire section 1 and the remote control section 2 are freely coupled or separated.

Further, in the above mentioned embodiment, the polypectomy instrument 100 in which the snare 3 is coupled as the actuator for resecting the polyp P of the stomach or the intestine is given as an example, but the present invention may be applied, in addition, to various remote controlled medical instruments such as, a body tissue collecting instrument in which a bioptome equipped with a sharp blade is coupled as the actuator for cutting and collecting the malignant or benign tissue of the body, and an internal foreign object extracting instrument in which a grasping forceps of for example, V-shape, a V-crocodile shape, open-mouthed shape, a basket-shape, a tripod-shape and the like is coupled as the actuator to extract the foreign object taken inside the body.

The invention claimed is:

1. A remote controlled medical instrument comprising a wire section inserted into a body and equipped with an actuator for treating internal objects at a front end, and a remote control section for controlling the actuator outside of the body; wherein
    the wire section includes,
    a wire coupled with the actuator at the front end thereof and
    a tube for passing the wire and the actuator therein in a freely entering and exiting manner; and wherein
    the remote control section includes,
    a rod-shaped main body having a hollow inside,
    an operating member, coupled to the main body so as to be slidable in a longitudinal direction of the main body, for entering and exiting the actuator into and from the tube by sliding, and
    a pinching mechanism, built in the main body and coupled to the operating member, for detachably pinching a rear end of the wire and including:
    a coupling member for coupling the operating member and the wire,
    a clip member, arranged on the coupling member, for pinching the wire, and
    a sliding member sliding independently from the coupling member in the longitudinal direction of the main body; and wherein
    the clip member pinches the wire in conjunction with the sliding of the sliding member in a first direction, and releases the wire in conjunction with the sliding of the sliding member in a second direction opposite to said first direction, the remote control section including a spring biasing said sliding member in said first direction.

2. The remote controlled medical instrument as claimed in claim 1, wherein
    the pinching mechanism is rotatably built in the main body with an axis of the longitudinal direction of the main body as a rotating center, and rotates the pinched wire and the actuator in conjunction with each other.

3. A remote controlled medical instrument comprising a wire section inserted into a body and equipped with an actuator for treating internal objects at a front end, and a remote control section for controlling the actuator outside of the body; wherein
the wire section includes,
a wire coupled with the actuator at the front end thereof; and
a tube for passing the wire and the actuator therein in a freely entering and exiting manner; and wherein
the remote control section includes,
a rod-shaped main body having a hollow inside,
an operating member, coupled to the main body so as to be slidable in a longitudinal direction of the main body, for entering and exiting the actuator into and from the tube by sliding, and
a pinching mechanism, in the main body and slidably retained on the operating member, for detachably pinching a rear end of the wire.

4. The remote controlled medical instrument of claim 3 wherein said operating member includes an operating member body having a centerline and an end and said pinching mechanism comprises a clip member having a first portion overlying and connected to said operating member body and a second portion biased away from said centerline.

5. The remote controlled medical instrument of claim 4 wherein said second portion extends beyond said operating member body end.

6. The remote controlled medical instrument of claim 4 wherein said pinching mechanism further includes a sliding member shiftable between a first position and a second position, said sliding member pressing said second portion toward said centerline when moving from said second position to said first position.

7. The remote controlled medical instrument of claim 3 wherein:
said operating member includes an operating member body having a centerline and an end; and
said pinching mechanism comprises first and second clip members each having a first portion overlying and connected to said operating member body and a second portion biased away from said centerline.

8. The remote controlled medical instrument of claim 7 wherein said second portions of said first and second clip members extend beyond said operating member body end.

9. The remote controlled medical instrument of claim 7 wherein said pinching mechanism further includes a sliding member shiftable between a first position and a second position, said sliding member pressing said second portions of said first and second clip members toward said centerline when moving from said second position to said first position.

10. A remote controlled medical instrument comprising:
a tube adapted to be inserted into a body and having a first end and a second end;
a wire extending through said tube and including a first end attached to a functional member at said tube first end and an attachment portion extending from said tube second end;
a remote control section connected to said tube second end for controlling the functional member from outside the body comprising a main body having a hollow inside,
an operating member, longitudinally slidably coupled to the main body, the operating member comprising an operating member body having an end, first and second clips each having a first portion overlaying and connected to said operating member body and a second portion extending beyond the end of the operating member body, the second portions being biased away from each other, and a sliding member retained on said operating member body and slidably shiftable between a first position pressing said second portions toward each other and a second position allowing said second portions to separate from each other.

11. The remote controlled medical instrument of claim 10 wherein said first and second clips each include a third portion between said first and second portions, said third portions overlying and biased away from said operating member body.

12. The remote controlled medical instrument of claim 11 wherein said third portions move toward said operating member body when said sliding member moves from said second position to said first position.

13. The remote controlled medical instrument of claim 10 wherein said sliding member is spring biased toward said first position.

14. The remote controlled medical instrument of claim 10 wherein said first clip first portion is spaced from said second clip first portion.

* * * * *